United States Patent
Gibbs et al.

(10) Patent No.: US 10,068,049 B2
(45) Date of Patent: *Sep. 4, 2018

(54) AUTOMATED FIDUCIAL MARKER PLANNING METHOD

(71) Applicant: Broncus Medical, Inc., Mountain View, CA (US)

(72) Inventors: Jason David Gibbs, State College, PA (US); Lav Rai, State College, PA (US); Henky Wibowo, Cupertino, CA (US)

(73) Assignee: BRONCUS MEDICAL, INC., San Jose, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/908,187

(22) Filed: Jun. 3, 2013

(65) Prior Publication Data
US 2013/0346051 A1 Dec. 26, 2013

Related U.S. Application Data

(63) Continuation of application No. 12/861,795, filed on Aug. 23, 2010, now Pat. No. 8,468,003.

(51) Int. Cl.
| | | |
|---|---|---|
| G06G 7/60 | (2006.01) | |
| A61B 5/05 | (2006.01) | |
| G06F 19/12 | (2011.01) | |
| G06T 19/00 | (2011.01) | |
| A61N 5/10 | (2006.01) | |
| A61B 34/10 | (2016.01) | |
| G16H 50/50 | (2018.01) | |
| G06F 19/00 | (2018.01) | |

(52) U.S. Cl.
CPC .............. *G06F 19/12* (2013.01); *A61B 34/10* (2016.02); *A61N 5/1049* (2013.01); *G06T 19/00* (2013.01); *G16H 50/50* (2018.01); *A61B 2034/107* (2016.02); *G06F 19/321* (2013.01); *G06F 19/3481* (2013.01); *G06T 2210/41* (2013.01)

(58) Field of Classification Search
None
See application file for complete search history.

(56) References Cited

U.S. PATENT DOCUMENTS

2008/0027313 A1 * 1/2008 Shachar ................ 600/424
2010/0069746 A1 * 3/2010 St. John ................ 600/426

OTHER PUBLICATIONS

Ananntham et al. Chest, 2007; 132:930-935.*

* cited by examiner

*Primary Examiner* — Michael L Borin
(74) *Attorney, Agent, or Firm* — Convergent Law Group LLP; Richard Batt

(57) ABSTRACT

A system and method are described for determining candidate fiducial marker locations in the vicinity of a lesion. Imaging information and data are input or received by the system and candidate marker locations are calculated and displayed to the physician. Additionally, interactive feedback may be provided to the physician for manually selected or identified sites. The physician may thus receive automatic real time feedback for a candidate fiducial marker location and adjust or accept a constellation of fiducial marker locations. 3D renderings of the airway tree, lesion, and marker constellations may be displayed.

18 Claims, 8 Drawing Sheets

AUTOMATED FIDUCIAL MARKER PLANNING METHOD

CROSS-REFERENCE TO RELATED APPLICATIONS

This is a continuation of U.S. patent application Ser. No. 12/861,795, filed Aug. 23, 2010, entitled "AUTOMATED FIDUCIAL MARKER PLANNING SYSTEM AND RELATED METHODS".

FIELD OF THE INVENTION

The present invention relates to systems and methods for use in radiation oncology and more particularly, to the planning and placement of fiducial markers in the vicinity of lesions to be treated.

BACKGROUND OF THE INVENTION

Fiducial markers are useful in various medical applications. In radiation oncology, for example, fiducial markers are placed within or around lesions so that a therapeutic radiation delivery device can track the respiratory motion of the lesion to be destroyed, thereby minimizing damage to healthy surrounding tissue. An example of a radiation delivery device is the Cyberknife® system (manufactured by Accuray Inc., Sunnyvale, Calif.).

Fiducial markers may be placed in a wide variety of anatomies. In certain anatomies such as the lungs, however, placing a fiducial marker is not straightforward even for skilled practitioners. Traditionally, thoracic fiducial placement was performed percutaneously under computed tomography (CT) guidance. However, physicians have reported a 20-40% incidence of pneumothorax during such procedures. See Prevost et al., Endovascular Coils As Lung Tumor Markers In Real-Time Tumor Tracking Stereotactic Radiotherapy: Preliminary Results, *European Radiology*, 2008. Pneumothorax is a serious adverse, potentially fatal, event.

A minimally invasive procedure to place fiducial markers at locations in the lung is desirable to lower the risk of the above referenced adverse events and to eliminate the need for CT guidance. However, identifying suitable locations for placing fiducial markers bronchoscopically is challenging because of, amongst other things, (1) the limited view provided by an endoscope or bronchoscope, (2) the uncertainty in the marker locations arising from the tidal motion of the lung, (3) the presence of various obstacles such as critical blood vessels in the path to a fiducial marker location, (4) the heterogeneity of the lungs (i.e. the presence of both airways and parenchyma) surrounding the target lesion, and (5) the limitations arising from the particular oncology application to be performed. A system and method that addresses the shortcomings identified above is therefore desired.

SUMMARY OF THE INVENTION

Systems and methods are described for determining candidate fiducial marker locations in the vicinity of a lesion. Imaging information and data are input or received by the system and candidate marker locations are automatically calculated and displayed to the physician. Additionally, interactive feedback may be provided to the physician for each manually selected or identified site. The physician may receive automatic real time feedback for a candidate fiducial marker location and adjust or accept individual or a constellation of fiducial marker locations.

The system includes a processor operable to identify at least one fiducial marker location based on various imaging and other data received or input to the processor. The system may include additional components such as but not limited to a memory, display, and a user input device. In one embodiment of the present invention, the components are incorporated into a computer, or laptop type computer.

In another embodiment, the processor is operable to remove any candidate locations near obstacles such as blood vessels and or to remove any candidate marker locations which would obstruct visualization of a selected candidate marker location.

In another embodiment, the processor is operable to automatically identify the candidate marker location based on analysis of a patient's breathing motion.

In another embodiment, the processor is operable to automatically identify the candidate marker location based on specific patient or treatment information selected from the group consisting of a patient or treatment-specific constraints and fiducial marker characteristics.

In another embodiment of the invention, candidate marker locations are ranked or valued based on location specific information. Desired locations or sites may be manually selected or accepted and the system may operate to automatically plan at least one route to the selected location.

A method for planning placement of markers in the vicinity of a target in a patient comprises determining a 3D model of a thoracic anatomy; determining a 3D model of a target in the vicinity of the thoracic anatomy; and automatically identifying at least one candidate marker location for placement of a marker based on information arising from the 3D model of the thoracic anatomy and the 3D model of the target.

In another embodiment, the method includes preparing a 3D model of an obstacle in the vicinity of the thoracic anatomy, and removing any candidate locations near the obstacle from the candidate marker location. The obstacle may be a blood vessel.

In another embodiment, the method includes automatically removing any candidate marker locations which would obstruct visualization of another selected candidate marker location.

In another embodiment, the identifying step is based on a patient's breathing motion, a treatment-specific constraint, or a marker characteristic.

In another embodiment, the method includes assigning location specific information to each of the candidate marker locations.

In another embodiment, the method includes determining at least one constellation of marker locations based on the location specific information, and wherein the constellation comprises at least two candidate marker locations.

In another embodiment, the method includes ranking each constellation based on the location specific information.

In another embodiment, the method includes selecting one or more selected locations from the at least one candidate marker location and displaying the at least one candidate marker location.

In another embodiment, the method includes automatically planning at least one route to the selected marker location.

In another embodiment, the method is performed in an airway tree and the target is a tissue such as a lesion.

In another embodiment, the method comprises identifying at least one candidate location in the vicinity of an airway wall.

In another embodiment, a system for identifying locations for placing markers in the vicinity of a target in a patient comprises a memory for storing image information of a thoracic anatomy and image information of a target in the thoracic anatomy; a user input device for manually identifying at least one candidate marker location; and a processor operable to automatically provide feedback regarding the at least one candidate marker location. The processor may be operable to determine a 3D airway tree model from the image information of a thoracic anatomy, and to determine a 3D target model from the image information of a target in the thoracic anatomy, and to send to a display the 3D airway tree model and the 3D target model.

In another embodiment, the processor is operable to determine a 3D obstacle model from the image information of the thoracic anatomy.

In another embodiment, the processor is operable to indicate whether the candidate location is in the vicinity of the obstacle.

In another embodiment, the processor is operable to provide feedback wherein the feedback is based on whether the candidate location would obstruct visualization of a previously selected marker location.

In another embodiment, the processor is operable to provide feedback wherein the feedback is based on a previously selected marker location, a patient's breathing motion, treatment-specific constraints, a marker characteristic, location of blood vessels, and/or the distance from the target.

In another embodiment, a method for identifying locations for placing markers in the vicinity of a target in a patient comprises receiving image information of a thoracic anatomy; receiving image information of a target in the vicinity of the thoracic anatomy; manually identifying at least one candidate marker location; and automatically providing feedback regarding the at least one candidate location.

In another embodiment, the identifying step comprises identifying the candidate location with a computer input device such as a mouse.

In another embodiment, the method further includes determining a 3D airway tree model from the image information of a thoracic anatomy, determining a 3D target model from the image information of a target in the thoracic anatomy, and displaying the 3D airway tree model and the 3D target model.

In another embodiment, the determining step includes determining an obstacle from the image information of the thoracic anatomy.

In another embodiment, the feedback is based on whether the candidate location is in the vicinity of the obstacle, on a previously selected marker location, on whether the candidate location would obstruct visualization of the previously selected marker location, on a patient's breathing motion, and/or on treatment-specific constraints.

The step of identifying may also include identifying a constellation or set of marker locations. Also, the step of providing automatic feedback may be performed by providing feedback regarding the constellation.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is to be appreciated that unless defined otherwise, all technical and scientific terms used herein have the same meaning as commonly understood by one of ordinary skill in the art to which this invention belongs.

Figure 1:
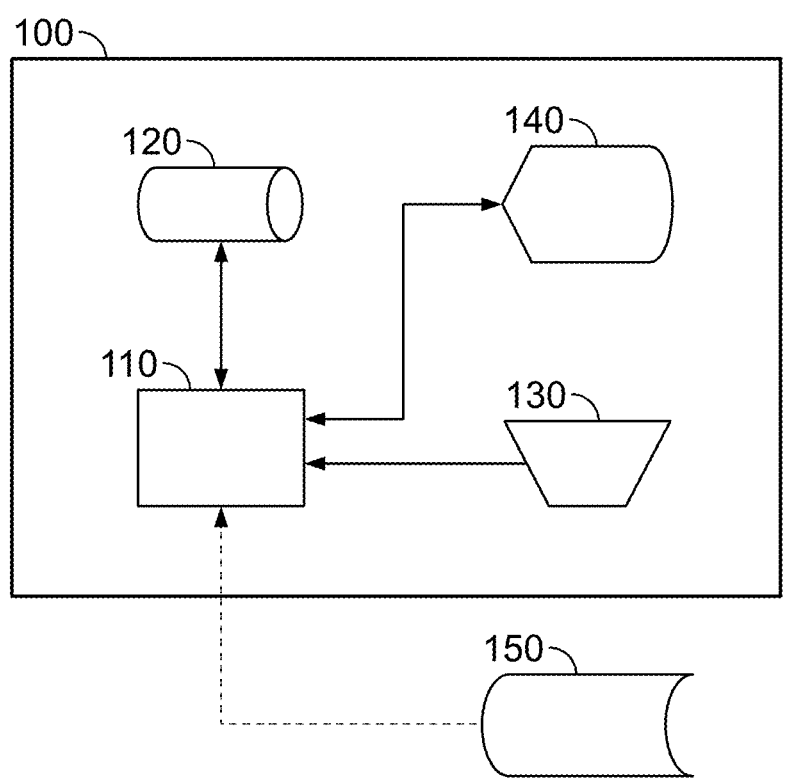
FIG. 1 is a block diagram of a fiducial marker location planning system.

FIG. 1 illustrates a system 100 for automatically identifying at least one and, more preferably, a plurality fiducial marker locations or constellation of marker locations.

The system 100 shown in FIG. 1 includes a processor 110 operable to determine the tissue marker locations based on various data and information as will be described in more detail below.

System 100 is shown having a memory device 120 which holds or stores information including imaging, device, marker, and procedural data. The system 100 shown in FIG. 1 includes a user input device 130 such as, for example, a keyboard, joystick, or mouse. The user input device allows a user such as the physician to add or input data and information as well as modify the marker location and to make notes in the files and records.

The system 100 shown in FIG. 1 also includes a display 140 which may present reports, data, images, results and models in various formats including without limitation graphical, tabular, and pictorial form.

It is to be understood, however, that although the system in FIG. 1 is shown with a memory 120 for receiving and storing various information the invention is not so limited. In an alternative embodiment the system may be configured to merely access a memory device such as a USB stick, a CD, or other media storage device.

In another embodiment the processor is connectable to a memory device 150 through the internet or through another communication line to access a network. For example, patient data CT scans may be stored on a server of a hospital and the processor of the instant application is adapted to access such data via a communication line and process the data.

Displays may be incorporated with the processor in an integrated system or the displays may cooperate with the processor from a remote location. A processor may be adapted to send or deliver data across a network to one or more displays or portable computer devices or smart phones such as the iphone® manufactured by Apple, Inc. Cupertino, Calif., United States. Indeed, although the computer system shown in FIG. 1 includes a number of various components incorporated into a system, the invention is not so limited. The invention is intended to be limited only as defined in the appended claims.

Figure 2A:
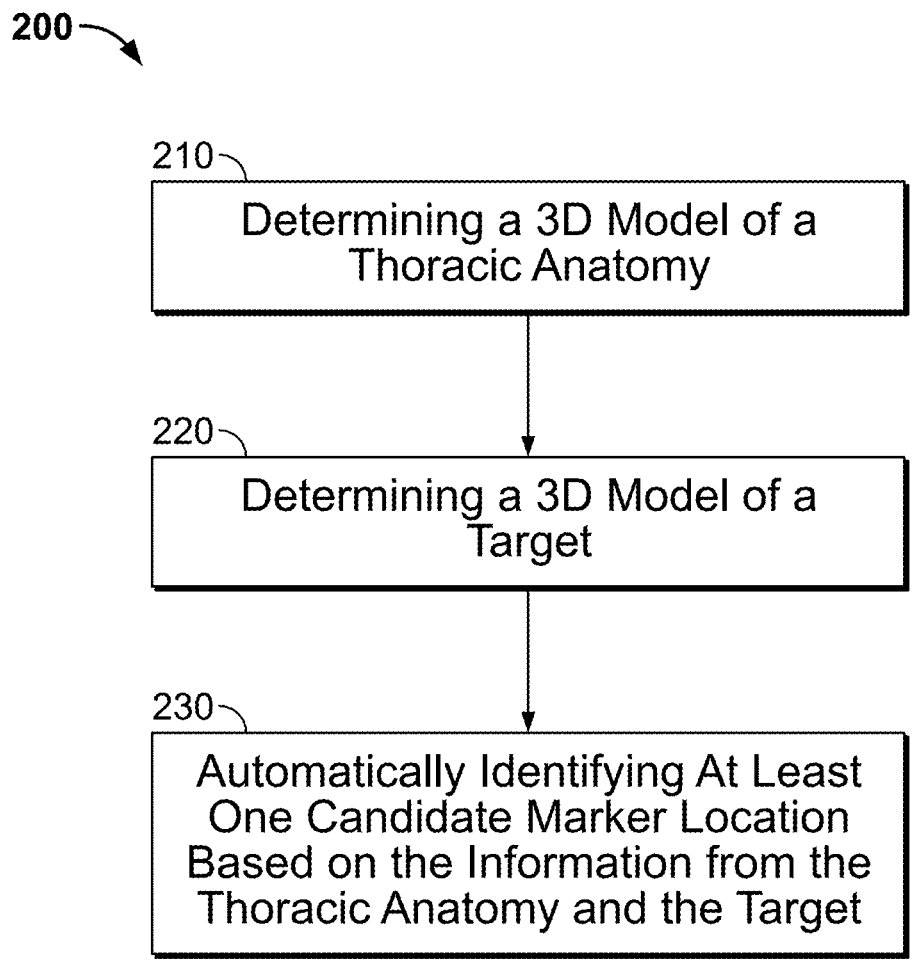
FIG. 2A shows steps for automatically planning fiducial marker locations.

FIG. 2A shows an overview for identifying candidate tissue marker locations. The steps may be carried out on a computer or system and include: step 210 determining a 3D model of a thoracic anatomy; step 220 determining a 3D model of a target, and step 230 automatically identifying a candidate tissue marker location based on the above requirements, models and information determined from the preceding steps.

Figure 2B:
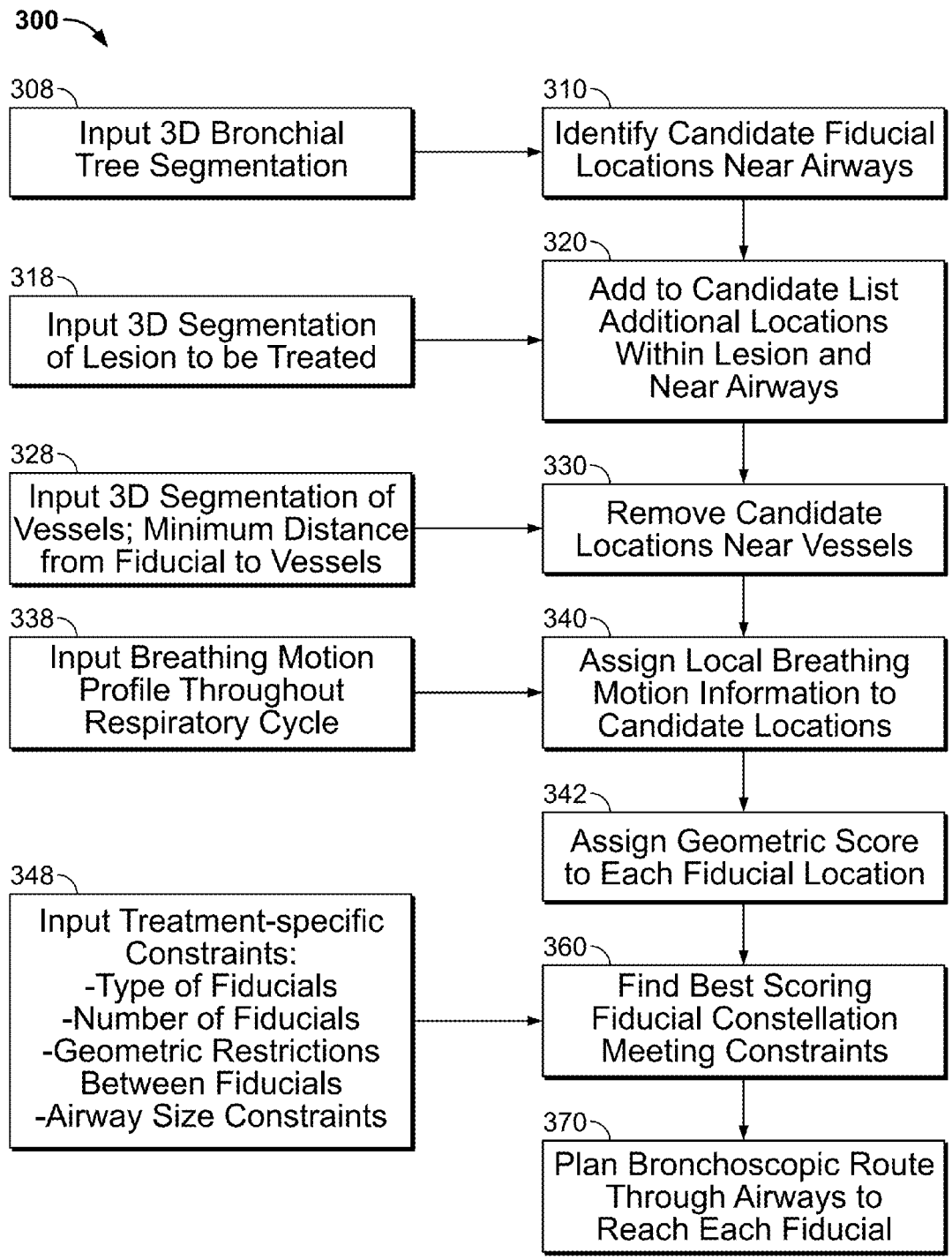
FIG. 2B shows steps for automatically planning a route to one or more fiducial marker locations.
Figure 3:
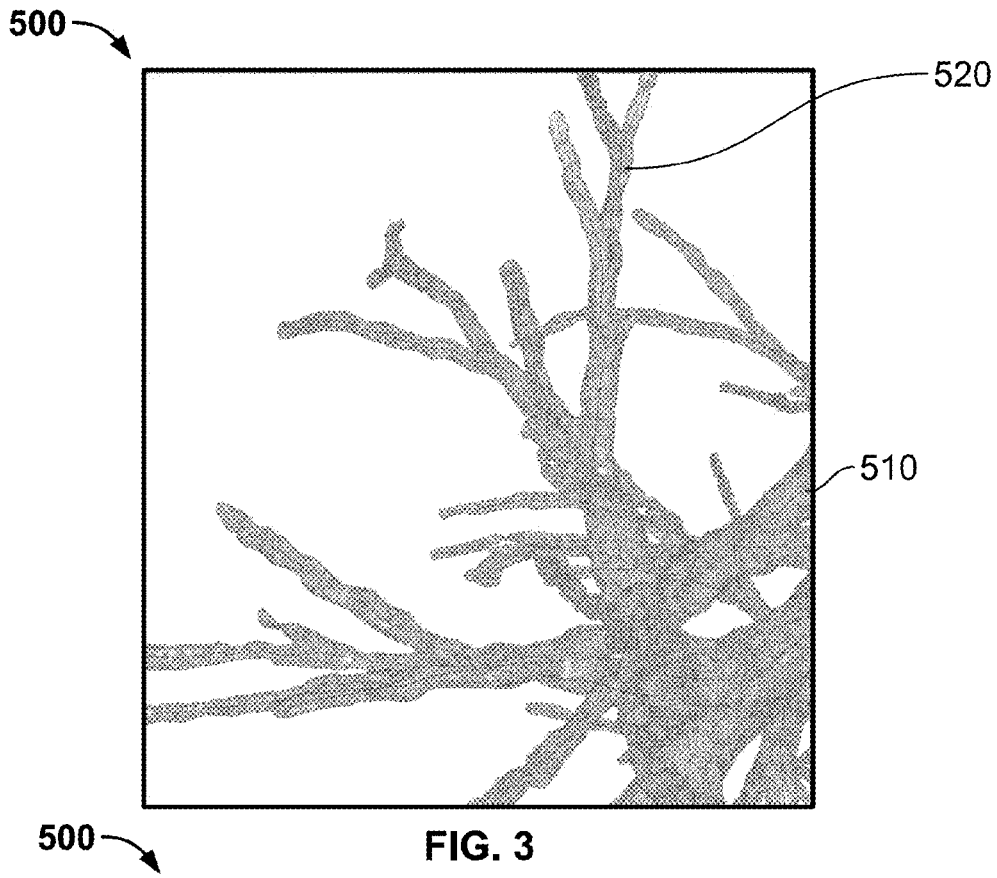
FIG. 3 shows an airway tree segmentation.

FIG. 2B shows another method or process to identify candidate fiducial marker locations and to plan a route to the fiducial marker locations. With reference to FIG. 2B, step 308 recites to input a 3D bronchial tree segmentation. The input may be provided, received, or determined based on available image data from a patient such as high resolution computed tomography (HRCT) scans. An example segmentation of a 3D model 500 of a bronchial tree is shown in FIG. 3. Reference numeral 510 indicates an airway and 520 indicates centerlines of the airways. An exemplary technique to determine a 3D model of a bronchial tree anatomy is disclosed in U.S. Patent Publication No. US 2006/0159328 entitled "Method and apparatus for airway detection and segmentation".

Though the figures refer to segmentation of the bronchial tree, the invention need not be so limited. A 3D segmentation of another anatomy such as the thoracic anatomy or an anatomical location outside of the thoracic anatomy may be input or determined in the present invention. Also, by use of the term "thoracic anatomy" it is meant to include without limitation the lungs, lymph nodes, chest cavity, vasculature, and other tissues and structures in and around the vicinity of the thoracic region.

With reference to FIG. 2B, step 310 recites to identify candidate fiducial locations near the airways identified in the preceding step 308. The distance from the airway wall may be selected in a range from 0 to 100 mm. In one embodiment, the candidate fiducial locations near the airways are about 1 to 3 mm from the airway walls.

Figure 4:
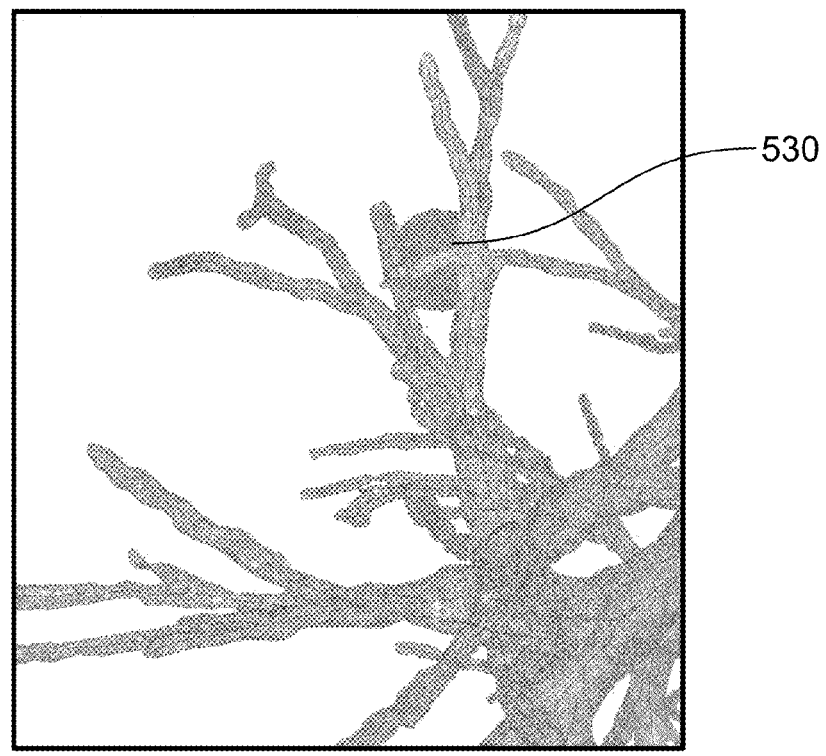
FIG. 4 shows the airway tree segmentation shown in FIG. 3 and a 3D segmentation of a lesion.

Step 318 recites inputting 3D segmentation of the lesion to be treated. Though the term "lesion" is recited in this step, the invention may include segmentation of another type of target. A target may include a wide variety of structures including without limitation a lymph node, tumor, or another tissue, deposit or object. FIG. 4 shows a 3D model of a lesion 530 in the lungs. An exemplary technique to determine a 3D model of a target in the thoracic anatomy is disclosed in U.S. Pat. No. 7,660,451 and entitled "System, method and apparatus for small pulmonary nodule computer aided diagnosis from computed tomography scans".

Figure 5A:
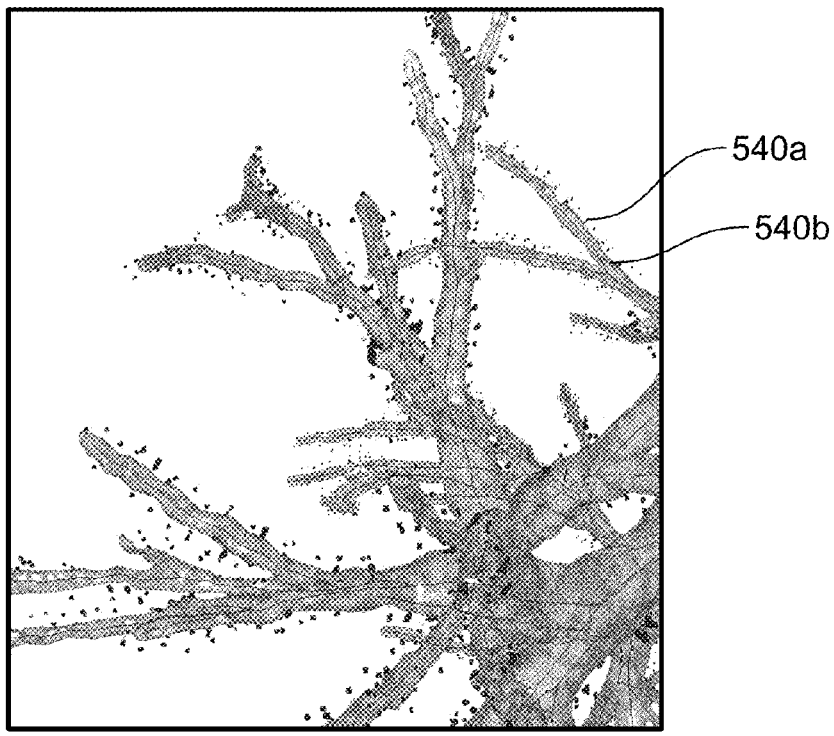
FIGS. 5A-5C show the airway tree segmentation shown in FIG. 2 and a plurality of candidate locations with those near blood vessels removed.

With reference to FIG. 2B, step 320 recites adding additional locations within the lesion and near the airways. Additional candidate locations may be added that are in the vicinity of the lesion or airways. The fiducial markers may be placed in close proximity to the lesion and preferably, but not necessarily, the maximum distance is in the range of 0 to 50 mm from the lesion or target. The closer the fiducials are to the lesion, the more accurately the fiducials will reflect the motion of the lesion during the breathing cycle. FIG. 5A illustrates a bronchial tree 500 comprising a plurality of candidate fiducial marker locations 540 along the airways and in the vicinity of the lesion.

Figure 5B:
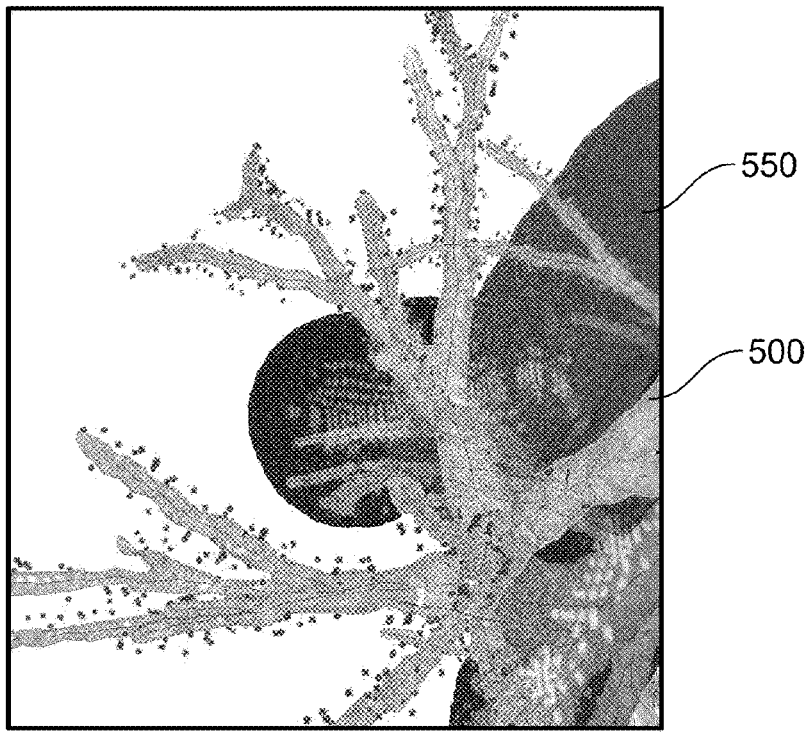

With reference to FIG. 2B, step 328 recites inputting a 3D segmentation of the vessels, namely, the blood vessels such as the pulmonary artery and aorta. FIG. 5B shows a 3D model of the vasculature 550 in the bronchial tree 500. An exemplary technique to determine a 3D model of vasculature in the thoracic anatomy is disclosed in U.S. Pat. No. 6,728,566 entitled "Vessel tracking and tree extraction method and apparatus".

Step 328 also recites inputting a minimum distance between the vessels and the fiducial to ensure the vessels are not injured. This may be carried out by the physician inputting information using a keyboard. Minimum distances may vary according to the physician and an exemplary range is from about 1 to 30 mm.

Figure 5C:
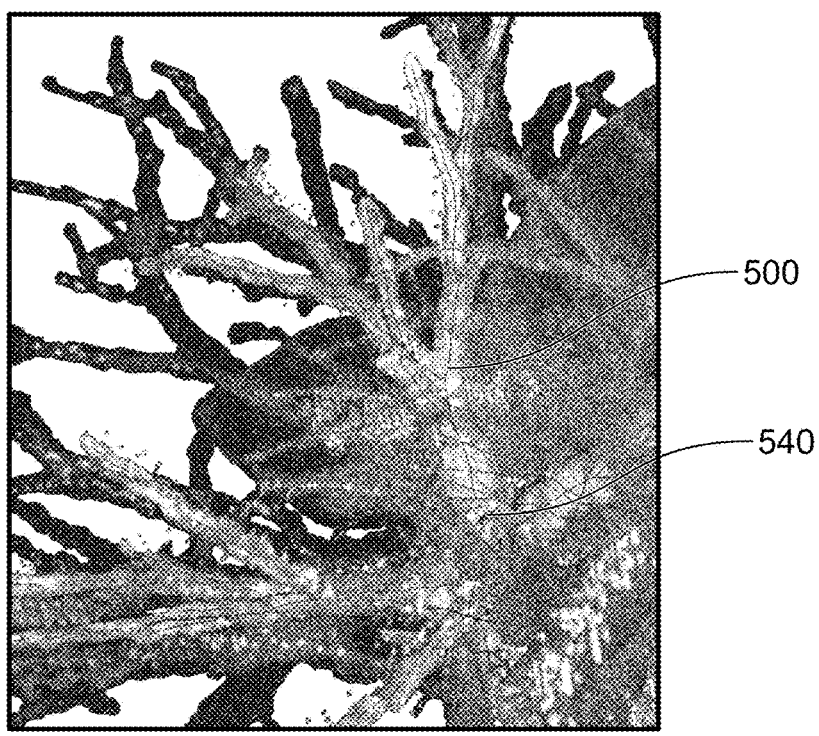
Figure 6:
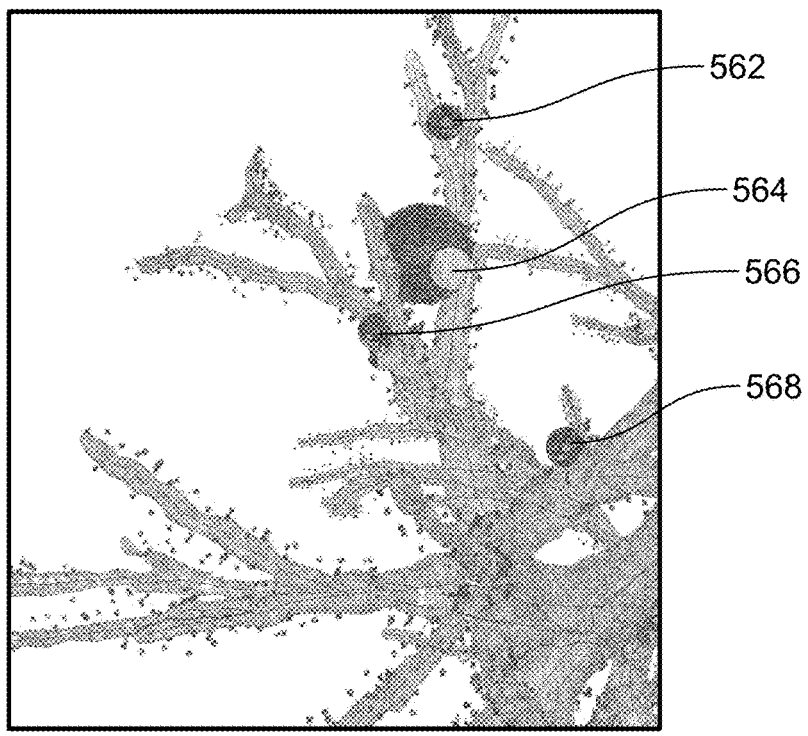
FIG. 6 shows the airway tree segmentation shown in FIG. 2 and a 3D segmentation of a lesion, and a fiducial marker constellation.

With reference to FIG. 2B, step 330 recites to remove candidate locations near the vessels or within the minimum distances described above. FIG. 5C illustrates a bronchial tree 500 comprising a plurality of candidate fiducial marker locations less a number of fiducial marker locations removed for being too close to the blood vessels.

With reference to FIG. 2B, step 338 recites inputting a breathing motion profile corresponding to the respiratory cycle of the patient. This may be input or received in the form of, for example, image data of the bronchial tree and airways at multiple points in time corresponding to inhalation, exhalation, and perhaps one or more time points between inspiration and expiration. The data may be processed to identify displacement of tissues and tissue surfaces. A review of the image data across multiple points in time serves to accurately show the breathing motion profile of the patient. An exemplary process for carrying this out is described in "Fast Deformable Registration on the GPU: A CUDA Implementation of Demons" by Pinar Muyan-Ozcelik, 2008 wherein the authors describe using a pair of CT scans acquired from the same patient, one at a full level of inspiration and the second at a full level of expiration. The deformable registration technique described in this paper gives the mapping of each discrete point within the lungs at from its geometric location at expiration to inspiration and from inspiration to expiration. From these mappings, the location of any region within the chest can be estimated at points during the breathing cycle.

Step 340 recites assigning local breathing motion information to candidate locations.

Step 342 recites assigning a score or geometrical score to each fiducial location. The score may be calculated by awarding higher values to those candidate marker locations having certain characteristics such as a close proximity to the target at individual points in the breathing cycle, or summing the scores at multiple points in the breathing cycle, thus awarding benefit to fiducial locations which remain consistently near the target throughout the breathing cycle.

Step 348 recites inputting various information and constraints. The constraints are described below and intended to be combined in any logical way. Not all described constraints are required to carry out the invention. However, one or more constraints may be combined if desired.

Constraints or input may be provided via an input device such as a keyboard or another means to add information or data to be considered and processed. Treatment-specific constraints may include, for example, the type of fiducial, the number of fiducials, geometric restrictions between fiducials, and airway size constraints. Some fiducials, for example, are designed to be placed in tissue, and others are designed to be anchored within cavities such as airways.

Fiducial constraints may include without limitation the size, material, model number, etc. Though the specific characteristics of a fiducial is desirable, in an alternative, default or atlas values may be input. Default values may be based on known fiducials. Examples of fiducial markers are gold rods measuring 0.8-1 mm in diameter by 3-7 mm in length (e.g., Product No. 351-1 manufactured by Best Medical International, Inc., Springfield, Va.).

Another constraint is the quantity and geometry of the fiducial markers. Preferably, there should be a sufficient number and appropriate geometry of fiducial markers in a given constellation to determine the relative geometry of the lesion with respect to the constellation. Since the fiducial markers are tracked by an imaging system, there may be additional requirements on the geometry of the fiducial marker constellation. The objective of the various requirements on the constellation geometry are to ensure that each fiducial can be separately resolved and tracked within the imaging system and thus provide geometric information about the target.

Another constraint or input is visualization. Namely, it is preferred that no fiducial should block the view during visualization of another fiducial. In the CyberKnife system, for example, the markers are tracked by two fluoroscopy units that are located on a 45-degree rotated axis with respect to the normal axial directions. For the best resolution within the system, pairs of markers preferably are not located such that multiple markers appear as a single marker in either fluoroscopy projection. That is, one fiducial marker preferably does not occlude another fiducial marker in either of the two fluoroscopy imaging planes. As such, the camera geometry and minimum separation distance between projected pairs of fiducial markers in the fluoroscopy imaging planes are additional inputs/constraints to the fiducial planning system.

Another constraint may include optimal separation distances or rules dictating the relative geometry between subsets of fiducial markers within the overall constellation. For instance, it has been reported that the Cyberknife system operates best with a minimal separation of at least 2 cm between fiducial markers. In this way, the tracking system is best able to resolve the position of each individual marker. These inter-fiducial marker distance requirements are additional inputs/constraints to the fiducial planning system. As mentioned herein, because of the requirements of external tracking systems, there may be significant separation required between fiducial markers. This separation may necessitate that the fiducial markers be implanted in healthy tissue at some distance from the lesion. The system may define "anchorable positions" such as tissue surrounding the airway tree but devoid of major blood vessels.

Anchorable positions may also be determined manually by the physician or by, for instance, an atlas of appropriate anchorable regions (such as lymph nodes). Such regions could be registered to the airway model or extracted directly from the patient-specific CT scan. Image processing subroutines and/or atlas based approaches for identifying appropriate anchor points outside the lesion are additional inputs/constraints to the fiducial planning system.

Yet another constraint is analysis of the motion of previously placed fiducial markers. More specifically, the motion of previously placed fiducials may be observed through the breathing cycle with respect to one another and with respect to the targeted lesion to provide feedback as to the quality of a particular constellation. Tolerances on the respiratory motion displacement disparity between fiducial pairs and specific points on the lesion (such as the center of mass) can be an additional input/constraint to the fiducial planning system.

With reference to FIG. 2B, step 360 recites finding a best scoring fiducial constellation or set of fiducial markers based on the constraints. Given the previously-described preferred constraints (e.g., the sites preferably surround the airway tree, the sites preferably are within the lesion, and in lymph nodes, that each fiducial site preferably shall be placed in an endoscopically or bronchoscopically accessible location (or accessible through another method that can be modeled), that each candidate location preferably shall contain tissue into which the fiducial can be anchored, and that obstacles are avoided during placement of the fiducial), the system can assign costs and benefits to the above requirements and then examine potential combinations of fiducial markers in different constellations.

Figure 7:
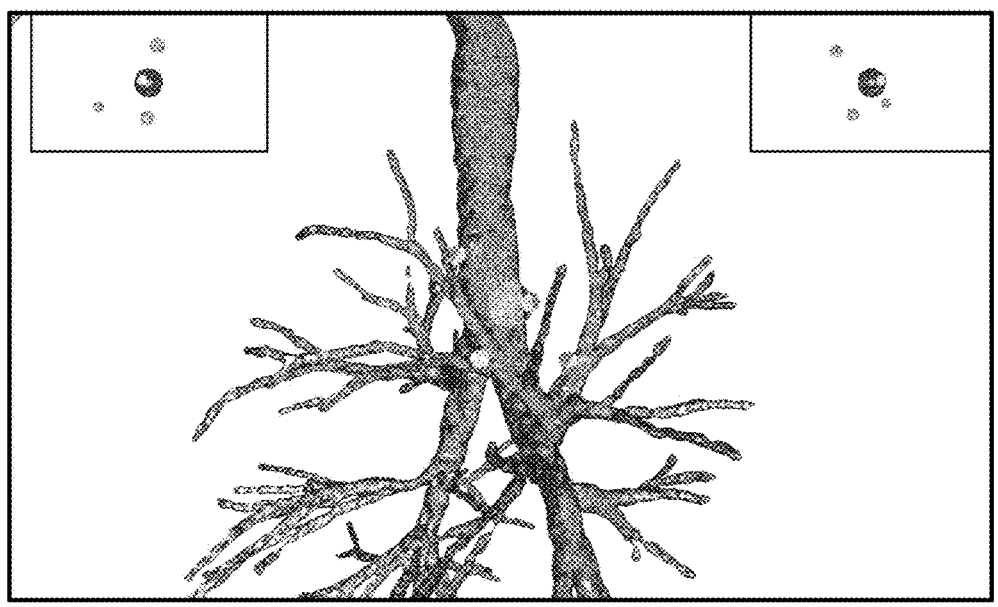
FIG. 7 shows a global virtual view of an airway tree, a fiducial constellation, and a lesion.

A total weighted combinatorial cost/benefit for a particular constellation may be determined or calculated. An example of a combinatorial cost/benefit algorithm is the genetic algorithm, which finds subsets of solution combinations (in this specific case, fiducial marker locations) from a large corpus of potential solutions as described by Goldberg in Genetic Algorithms in Search, Optimization, and Machine Learning, 1989. The system may then return the constellation (or constellations) with the best cost/benefit characteristics. The individual components within the cost/benefit analysis can be weighted differently dependent upon the requirements of the treatment delivery system and the physician preferences. An example illustration of a constellation is shown in FIG. 7. The constellation shown in FIG. 7 includes four separate markers.

Additionally, the constellation may be modified by the physician. Marker locations may be adjusted, selected or eliminated. The method 300 may calculate and suggest one or more candidate tissue marker locations. The markers may be accepted, and displayed on a monitor or printed in a report.

Figure 8:
FIG. 8 shows the airway tree shown in FIG. 7 and a path to one fiducial marker location of the fiducial marker constellation.

The last step shown in FIG. 3 (Step 370) recites planning a bronchoscopic route through the airways to reach the fiducial marker location. A technique to plan the route to a target region of interest (namely, the selected fiducial marker location) is described in US Patent Publication No. 20080183073 to Higgins et al. See also LUNGPOINT® manufactured by Broncus Technologies, Inc. Mountain View, Calif. An example illustration of a route 830 through the airways 820 to a target tissue marker location 810 is shown in FIG. 8. The above described method receives imaging data of the thoracic anatomy and lesion, and automatically determines an optimal constellation of fiducial marker locations. The method or system then may provide one or more endoscopic routes to the preferred locations.

Figure 2C:
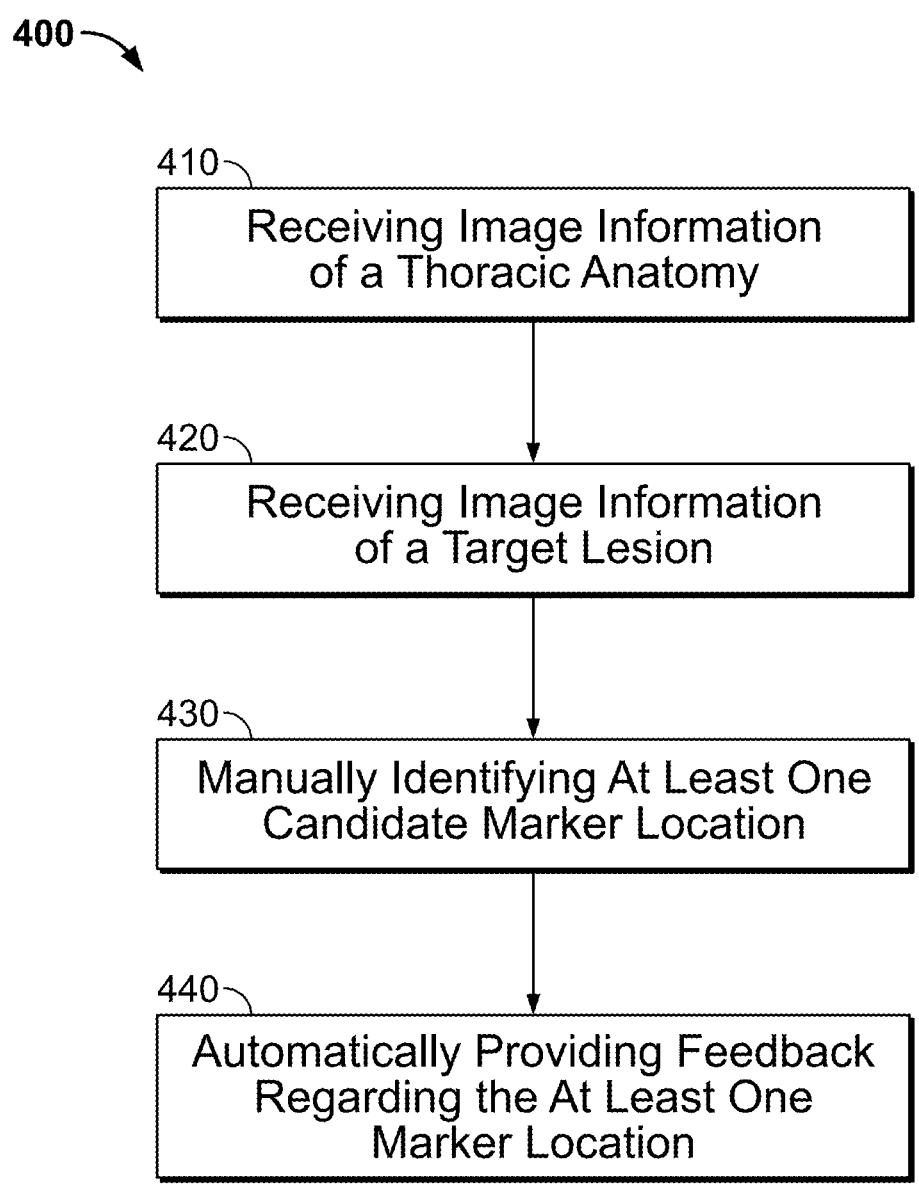
FIG. 2C shows steps for providing feedback to a physician for manually selected fiducial marker locations.

FIG. 2C shows an overview of a method 400 to provide a physician interactive feedback in real time for identified fiducial marker locations. With reference to FIG. 2C, step 410 recites receiving the image information of the thoracic anatomy. This step is similar to that described above in connection with FIG. 2B.

Step 420 recites receiving the image information of the target lesion. This step is also similar to that described above in connection with FIG. 2B. Further, the lesion or target may be outlined by the user with a tool. An example tool is the livewire or spherical tools in LungPoint® referred to above and as described in Lu et al. in Interactive Segmentation based on the Live Wire for 3D CT Chest Image Analysis.

Step 430 recites manually identifying at least one candidate marker location. This step may be carried out with an input device such as a mouse or keyboard. For example, a doctor may hover and double click a computer mouse over a certain area of the 3D segmentation or model of the lung and lesion.

Step 440 recites automatically providing feedback regarding the at least one marker location. By applying one or more of the constraints and algorithms described above in connection with FIGS. 2A and 2B, the method and system may provide feedback for a given set of user-selected fiducial markers.

The automatic feedback can be computed in real time and comprises quantitative data detailing at least a portion of the information described above. The physician can query different 3D locations by hovering the mouse over potential fiducial target locations and be provided with numerical quantities of the above constraints. Examples of numerical quantities include without limitation fiducial type, model number, distance to lesion, distance to blood vessel, anchorability, distance between fiducials, and endoscopic accessibility.

Additionally, constraints and requirements that fail can be highlighted with different formatting to draw attention to potential problems.

The fiducial markers may be displayed in 3D renderings with respect to the targeted lesion.

The projections of the lesions in the orthogonal fluoroscopy projections (e.g., Cyberknife fluoroscopy projections) can be displayed in real-time as a potential fiducial is placed to provide a visual representation of the distances between the projected fiducials. A virtual representation of fiducials in this manner is provided.

Other modifications and variations can be made to the disclosed embodiments without departing from the subject invention. For example, the quantitative and visual feedback provided by this method can be used in conjunction with non-bronchoscopic fiducial placement techniques (such as transthoracic needle placement). Many of the underlying requirements of the arrangement of the fiducials with respect to the imaging and tracking system remains the same, regardless of the placement technique.

We claim:

1. A computer-implemented method for providing visually enhanced, real-time feedback to assist a physician identify suitable candidate locations for placing markers in the vicinity of a target in a patient prior to performing a medical procedure, the method comprising:
    receiving image information of a thoracic anatomy of the patient;
    receiving image information of a target in the vicinity of the thoracic anatomy;
    identifying a constellation by identifying a plurality of candidate marker locations in at least one of the image information of the thoracic anatomy and the image information of the target;
    automatically providing feedback, in real time, including providing an enhanced visual representation of the plurality of candidate marker locations defining the constellation; and wherein the step of automatically providing feedback is based on (a) computing a score on a computer system, the computer system including a processor operable to compute the score for each of said candidate marker locations and for the constellation as a whole, and wherein the score is based on at least one constraint, and (b) displaying the at least one constraint in the enhanced visual representation; and wherein the step of identifying is performed prior to performing the medical procedure; and
    adjusting at least one candidate marker location of the constellation to a suitable location in the image information of the thoracic anatomy and target based on said automatic feedback and enhanced visual representation.

2. The method of claim 1 wherein the identifying step comprises manually identifying the candidate location with a computer input device.

3. The method of claim 2 comprising determining a 3D airway tree model from the image information of a thoracic anatomy, determining a 3D target model from the image information of a target in said thoracic anatomy, and displaying said 3D airway tree model and said 3D target model.

4. The method of claim 1 comprising determining an obstacle from the image information of the thoracic anatomy.

5. The method of claim 4 wherein the feedback includes indicating the candidate location is in the vicinity of the obstacle.

6. The method of claim 1 wherein the at least one constraint comprises whether said candidate location would obstruct visualization of a previously selected marker location.

7. The method of claim 1 wherein the at least one constraint comprises a patient's breathing motion.

8. The method of claim 1 wherein the at least one constraint comprises treatment-specific constraints.

9. The method of claim 1 wherein the at least one constraint comprises a marker characteristic.

10. The method of claim 1 wherein the identifying includes identifying a constellation comprising four candidate marker locations.

11. The method of claim 10 wherein the step of providing feedback is performed by providing feedback regarding the constellation.

12. The method of claim 1 wherein the constraint comprises the degree to which the at least one candidate marker location is anchorable.

13. The method of claim 12 wherein the at least one constraint further comprises a distance between the candidate marker location and the target.

14. The method of claim 1 wherein the computing step comprises computing a virtual 3D fiducial marker.

15. The method of claim 14 wherein the computing step comprises computing a quantitative data set displayable in combination with the virtual 3D marker.

16. The method of claim 1 wherein the adjusting step is performed by the physician.

17. The method of claim 1 wherein the computing step comprises computing a total weighted combinatorial cost/benefit.

18. A medical procedure planning method for providing visually enhanced, real-time feedback to assist a physician identify suitable candidate locations for placing markers in the vicinity of a target in a patient prior to performing the medical procedure, the method comprising:
    receiving image information of a thoracic anatomy of the patient;
    receiving image information of a target in the vicinity of the thoracic anatomy;
    identifying a constellation by identifying a plurality of candidate marker locations in at least one of the image information of the thoracic anatomy and the image information of the target;
    computing a score on a computer system for each of said candidate marker locations and for the constellation as a whole, and wherein the score is based on at least one constraint;
    displaying an enhanced visual representation of the thoracic anatomy, target, and constellation based on the computing step; and
    adjusting at least one candidate marker location of the constellation to a suitable location in the image information of the thoracic anatomy and target.

* * * * *